(12) United States Patent
Bruce et al.

(10) Patent No.: US 8,679,083 B2
(45) Date of Patent: Mar. 25, 2014

(54) REUSABLE BREAST SHIELD

(76) Inventors: Tina Bruce, Cary, NC (US); Charles J. Pawloski, Cary, NC (US)

(*) Notice: Subject to any disclaimer, the term of this patent is extended or adjusted under 35 U.S.C. 154(b) by 4 days.

(21) Appl. No.: 13/233,951

(22) Filed: Sep. 15, 2011

(65) Prior Publication Data

US 2012/0005799 A1    Jan. 12, 2012

Related U.S. Application Data

(63) Continuation of application No. 10/524,130, filed as application No. PCT/US02/18976 on Jun. 14, 2002, now Pat. No. 8,038,660.

(51) Int. Cl.
- *A61J 13/00* (2006.01)
- *A41C 3/00* (2006.01)
- *A41C 3/10* (2006.01)

(52) U.S. Cl.
USPC ............. 604/346; 128/890; 450/37; 450/57; 450/81

(58) Field of Classification Search
USPC .............. 604/346; 128/890; 450/37, 57, 81
See application file for complete search history.

(56) References Cited

U.S. PATENT DOCUMENTS

| | | | | |
|---|---|---|---|---|
| 2,054,491 | A  * | 9/1936 | Tynan | 604/346 |
| 6,200,195 | B1 * | 3/2001 | Furuno et al. | 450/81 |
| 6,419,548 | B1 * | 7/2002 | Wittes et al. | 450/57 |

* cited by examiner

*Primary Examiner* — Jacqueline F. Stephens
(74) *Attorney, Agent, or Firm* — Coats & Bennett, P.L.L.C.

(57) ABSTRACT

A reusable, washable breast shield for use by lactating women. The shield may include an inner layer and an outer layer. The shield may be placed against the breast of the user and may be held in place with an article of clothing or may be used without supporting clothing.

18 Claims, 3 Drawing Sheets

REUSABLE BREAST SHIELD

RELATED APPLICATION

The present application is a continuation of co-pending U.S. patent application Ser. No. 10/524,130, which is hereby incorporated by reference in its entirety.

BACKGROUND OF THE INVENTION

The present invention relates to an apparatus for controlling leakage of lactating fluid in human females. Specifically, this invention is a thin, multi-layered silicone compound based shield that conforms to the shape of the breast.

DESCRIPTION OF THE RELATED ART

Nursing and pregnant human females often experience spontaneous "let-down" and leakage of milk from their breasts. Leakage can be significant enough to bleed through undergarments and stain exterior clothing. This presents a problem of discomfort, embarrassment, inconvenience and sometimes even expense because of stained clothing. Leakage has typically been dealt with by the use of absorbent pads, or absorbent pads in combination with a liquid impervious barrier. Devices incorporating the use of absorbent pads are disadvantageous in that they create a bulky, conspicuous and unnatural look. Devices that currently define the art are often not reusable because of manufacturing design, and if reusable, must be laundered and dried presenting a problem with "downtime" requiring the user to purchase up to a dozen pair.

Breast shields incorporating the use of absorbent pads do not readily adjust to the shape of the breast of the user. The unsightly look imparted to the wearer and the bulk of breast shields using absorbent pads is a particular problem if a lactating woman desires to wear fitted, light textured or colored, or fine clothing such as an evening dress. Postpartum women are often highly conscious of their appearance and with great reluctance use a product that makes them look lumpy and malformed.

Breast shields using absorbent pads are by their nature opaque and are noticeable through light or semi-sheer garments. A breast shield with an absorbent pad used beneath such garments tends to make a woman self-conscious with a detrimental effect upon self-esteem. Breast shields that use absorbent pads are generally constructed with an absorbent layer near the skin of the wearer, with a liquid impervious layer between the absorbent pad and the outer clothing of the wearer. This arrangement traps the liquid against the body of the wearer causing discomfort or skin irritation. A frequent complaint of users of absorbent nursing pads is the discomfort experienced in having a cold liquid trapped against the skin. It is therefore advantageous to prevent or severely restrict the amount of breast milk leakage (BML) rather than collect it in a pad.

It is well known that a slight direct pressure to the nipple can control and limit leakage. Such a device incorporating this knowledge is disclosed in U.S. Pat. No. 5,394,899 issued to Morrisey et al. However, this type of device is also bulky, presenting an unnatural shape for the breast and uses an absorptive and opaque component. Therefore, there exists a need for a device that can severely limit or eliminate BML and prevent transmission of lactating fluid through undergarments to exterior clothing that is reusable, sanitary, washable, and further does not add bulk to the breast profile, and does not change the shape of the breast. There further exists a need for a device that can control spontaneous BML that can be worn under light and semi-sheer garments with little or no noticeability.

A frequent complaint of lactating women is the unsuitability of prior art nursing pads for use under swimwear. Nursing pads that are absorbent become saturated upon immersion of the wearer in water, rendering them useless. Also, the bulkiness of prior art nursing pads is particularly noticeable under swimwear. There exists a need for a nursing pad or breast shield that can be immersed in water, still function and be unnoticeable.

One of the common problems associated with breast shields is their tendency to slip out of place inside the clothing of the wearer. This problem has been overcome in the prior art by the use of adhesives, or by providing a rough frictional surface as an additional layer on the exterior of the device. However, this is not a completely satisfactory solution, as the addition of any layer to a breast shield exacerbates the problem of bulkiness. Also, adhesives frequently irritate the skin. Therefore, a need exists for a device that will stay in place without the use of adhesives, and for one that can be used without a bra to hold it in place.

SUMMARY OF THE INVENTION

The present invention relates to a device for controlling human lactation. The device comprises a thin, flexible and breathable, liquid impervious multi-layered shield that readily conforms to the shape of a human breast. The device can be used in conjunction with a bra to assist in shaping the shield and providing additional pressure against the nipple of the user to prevent spontaneous BML. The shield is a thin membrane having in inner surface and an outer surface. The shield is constructed of a material that is sufficiently stretchy in any direction so that a moderate pressure forces it to conform to the shape of a human breast. The shield has a tacky inner surface that allows it to remain in position without the use of adhesives or having to be attached to an outer garment such as a bra. The shield is pre-formed to present an elliptical surface in cross section, enabling it to more closely conform to the shape of a human breast. The shield material is also sufficiently translucent as to be almost invisible underneath clothing. The thickness of the shield is such that virtually no additional bulk is added to the breast profile of the wearer.

Testing of the present invention has indicated that leakage is significantly reduced if not eliminated altogether, and any leakage that does occur is contained. In one embodiment of the present invention the construction of the shield allows it to be used without a brassiere. The shield is used by first placing the shield against the nipple and depressing the nipple; then pressing the shield against the surrounding skin. The inherent tackiness of silicone rubber compounds of low durometer keeps the shield in contact with the skin without the use of adhesives. This gives nursing women freedom from having to wear a brassiere twenty-four hours a day. The shield also provides insulative properties, keeping the covered area warm; a distinct advantage in comfort over an absorptive nursing pad.

A variety of reusable breast shields are sized to cover a nipple, areola, and surrounding breast area of a human female. The breast shield may include a silicone rubber body with an inner layer having a thickness of between 10 and 20 mils and an outer layer. The body may have a total thickness of 20-90 mils. The breast shield may include a silicone rubber body with a first layer and a second layer. The first layer may have a smaller thickness than the second layer. The silicone rubber body may have an elliptical shape. The breast shield may include a two layer silicone rubber body with an inner layer and an outer layer. The inner layer may have a smaller thickness than the outer layer. A central area may have a greater thickness than the outer edge.

The present invention is also directed toward a method of controlling BML that utilizes the shield with a brassiere. The method includes the steps of placing the shield into the cup of a brassiere, securing the shield in place using an appropriate adhesive, and placing the brassiere on the wearer. The device and method of the present invention provide a convenient, economical, sanitary and attractive way to prevent leakage of lactating fluid on to the exterior clothing of the wearer. It is anticipated that the device of the present invention can be incorporated into a manufactured brassiere, by providing the instant invention with a fabric incorporated into or laminated onto the outer frame.

Although the present invention is designed to accommodate the needs of lactating women, it may be used by non-lactating women to help shape and support the breast and to prevent conspicuous noticeability of nipple erectile tissue in cold weather.

Accordingly, it is a principal object of the present invention to provide a device that will prevent spontaneous leakage of lactating fluid that does not require the use of an absorbent material. It is a further object of the present invention to provide a device for preventing spontaneous BML that is economical, washable, reusable and sanitary. It is a still further object of the present invention to provide a device that prevents the leakage of lactating fluid to the outer garments of the wearer that conforms to the shape of the breasts of the wearer and that is unnoticeable underneath clothing, It is a still further object of the present invention to provide a device that prevents the leakage of lactating fluid that will adhere to the skin of the wearer without the use of adhesives and that may be utilized with or without supporting outer clothing such as a brassiere.

These and other objects of the present invention will become readily apparent upon further review of the following specification and drawings.

DETAILED DESCRIPTION OF THE PREFERRED EMBODIMENT

Figure 1:
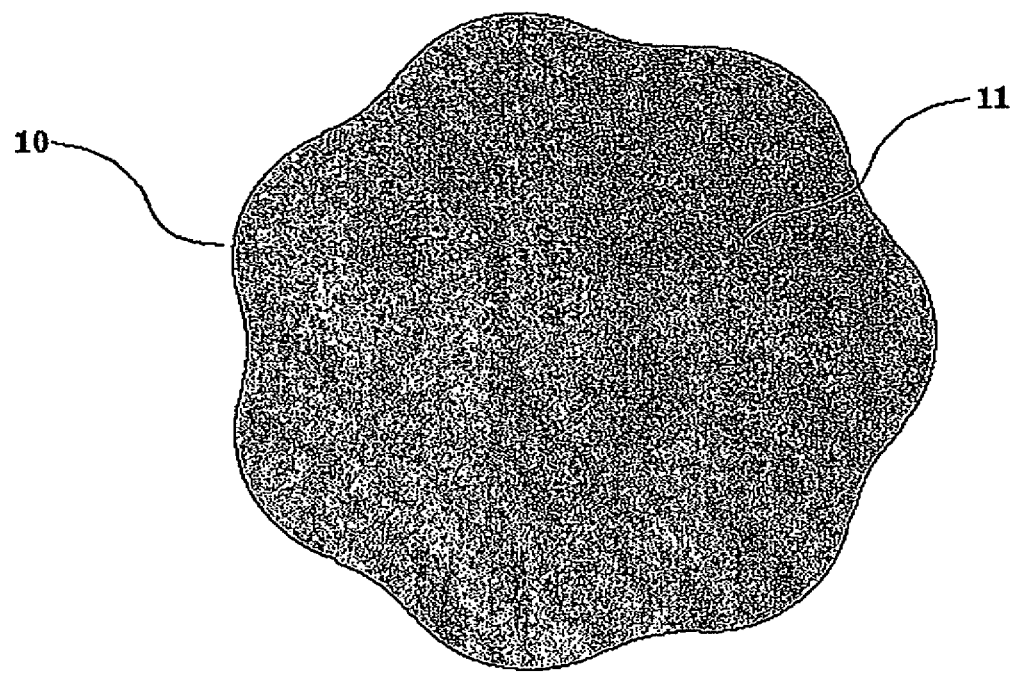
FIG. 1 is a top view of the shield according to the present invention, showing the exterior or non-body contacting surface.

Referring to FIG. 1, a shield of the present invention can be seen generally at 10. In a preferred embodiment, the shield 10 is a duel durometer laminated structure; the individual layers are manufactured from silicon rubber compounds. The shield may be constructed of other materials such as polyvinyl chloride (PVC) or polyurethane (PU), but design testing has shown that silicon rubber compounds provide an inherent flexibility, stretch and surface tension that enhances the functionality of the device. In a preferred embodiment, the shield 10 is essentially oval or circular including decorative edges, however other geometrical shapes may be used without affecting the functionality of the device. In particular, it is anticipated that the device would be constructed so that it could be trimmed to fit under specialty clothing such as a strapless evening gown. Other embodiments anticipate the use of decorative geometrical shapes such as flowers.

The shield 10 may be manufactured from a range of silicon rubber compounds as are well known in the art. Silicone rubbers exhibit a resistance to deformity that is expressed in durometers. The lower the durometer, the softer the material is and the less resistance the material exhibits to deformation. A low durometer number is also an indication of the material's relative tackiness. A silicone rubber's durometer and the device thickness control the relative stretchiness of the device; the durometer and smoothness of the part also reflect in the surface tension and tackiness of the material.

In a preferred embodiment, the shield is constructed of two layers, an outer layer of a higher durometer silicone compound and an inner layer of a lower durometer silicone compound. Other embodiments anticipate the use of a single layer membrane. Testing has shown that silicone rubbers also exhibit a resistance to lateral stresses and tearing that increase with thickness. The thicker the shield, the more resistant to tearing it is. The minimal thickness of the shield 10 is such that it will not tear when in use. Testing has shown that the shield 10 is functional at thickness less than 100 mils. However, when the shield 10 is manufactured at small thicknesses, it becomes difficult to handle and tends to fold over and stick to its self. Testing has shown that a thickness range of 20 to 90 mils works well for a consumer product.

Feedback from test subjects has indicated that some women prefer an extremely tacky inner surface, and some do not. In particular, testing has indicated that the device, when constructed of laminated layers of silicone compounds where the inner membrane is very tacky and the outer membrane or shell is less tacky, is particularly suitable for use without supporting clothing, and may be used as such when the wearer is sleeping. Feedback has also indicated that a single layered device of a higher durometer is functional for use under formal wear, where the outer clothing supports the device. A further advantage of the single layered device, shown in testing, is its tendency to shape the breast and to prevent the erectile tissue of the nipple from protruding if the wearer becomes chilled.

In one embodiment, the present invention can be provided to the user in a kit form allowing the user to incorporate the shield 10 into an existing article of clothing. It is anticipated that a clothing manufacturer can incorporate the present invention into an article of clothing. In such a case, the shield 10 could be made thinner, as machine handling would probably be able to overcome the difficulties encountered by an "at-home" installer.

In some embodiments, the shield 10 has no inherent color other than being slightly translucent. Other embodiments of the invention anticipate the use of color additives to the shield 10, as are well known in the art. Such color additives may be present to more closely match the skin tone of the wearer or to provide a decorative effect.

It is anticipated that the invention will be practiced by supplying the consumer with a range of diameters or sizes for the shield as well as colors. Large breasted women may require a large shield, and vice versa. In a preferred embodiment, the shield 10 has a diameter of approximately 3.7 inches.

Figure 2:
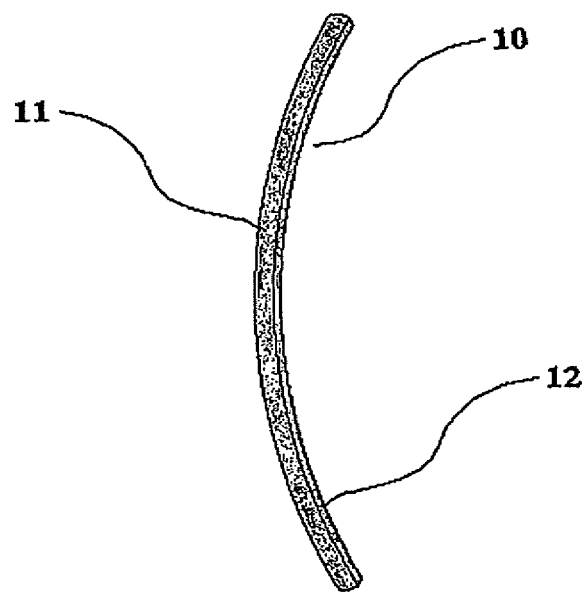
FIG. 2 is a side view of the shield according to the present invention, showing the shield in cross-section.

Referring now to FIG. 2, an exterior frame 11 and an interior coating 12 of the shield 10 can be seen. The exterior frame 11 comprises a silicone rubber compound of a comparatively high durometer versus the interior coating 12. In a preferred embodiment, the exterior frame 11 comprises injection molding grade silicone rubber compounds with a durometer between 0 and 100 using the Shore A scale. Testing has indicated that the exterior frame 11 is sufficiently stiff at 100 durometer Shore A, although in cases where more stiffness is desired, the exterior frame 11 may exceed 100 durometer Shore A. The exterior frame 11 will generally be between 10 mil and 70 mils thick, although for specific applications where greater stability or stiffness is required, the exterior frame may be thicker than 70 mils. Similarly, designs where maximum flexibility and deformability is desired, the exterior frame may be thinner than 10 mils.

Referring to FIG. 2, an inner membrane 12 of the shield 10 may be seen. In general, inner membrane 12 has no appreciable surface roughness. The smoothness of inner membrane 12 facilitates adherence of the shield 10 to the breasts. The lack of any appreciable surface roughness ensures a high coefficient of surface friction and eliminates pathways for leakage to the edge of the shield 10. The inner membrane 12 comprises silicone rubber compounds of a relatively low durometer as compared to the exterior frame 11. In a preferred embodiment, the inner membrane 12 comprises silicone rubber compounds that are 10 durometer or less. In other embodiments, the inner membrane 12 comprises silicone rubber compounds that range from a gel (0 durometer or below, Shore A), to 10 durometer. Also in FIG. 2, the curvature of the shield 10 may be seen. In a preferred embodiment, the shield 10 has an elliptical curvature, approximately 3.7 inches in diameter, and approximately 0.5 inches deep. It is anticipated that because of the flexibility of the silicone compounds that this design will suit most wearers however, other sizes and curvatures are anticipated. In particular, it is anticipated that the shield 10 may be sized so that it covers only the center portion of a breast, the nipple and areola area. In such an embodiment, the shield 10 may be as small as one inch in diameter or smaller.

Figure 3:
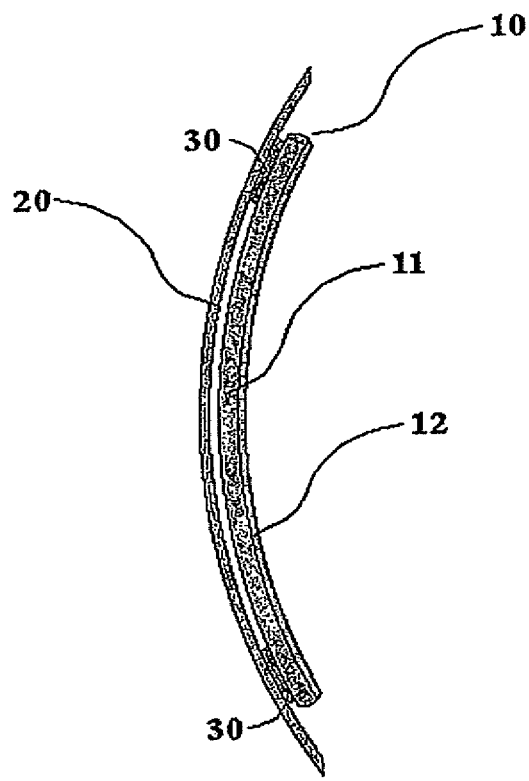
FIG. 3 is a view of the shield according to the present invention showing the shield secured into a brassiere.

Referring now to FIG. 3, the shield 10 is shown as having been secured by a user into a brassiere 20. In a preferred embodiment, the shield 10 is supplied in a kit to the end-user. The kit will contain an appropriate adhesive 30 as is well known in the art, allowing the shield 10 to be secured within the brassiere 20. This allows the user to "custom fit" the shield 10, ensuring maximum effectiveness.

Figure 4:
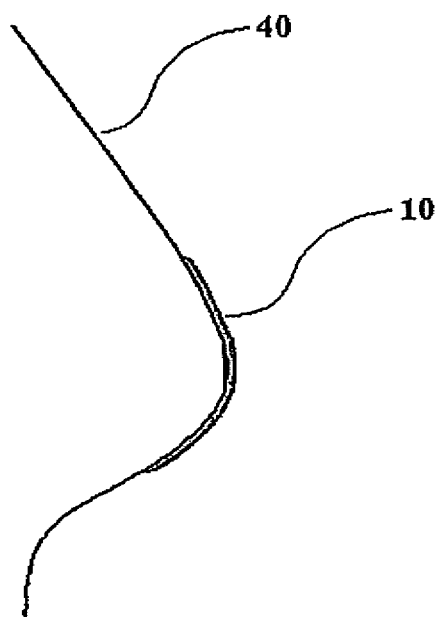
FIG. 4 is a view of the shield in use.

Referring now to FIG. 4, the shield 10 is shown as used in place on a breast 40.

Figure 5:
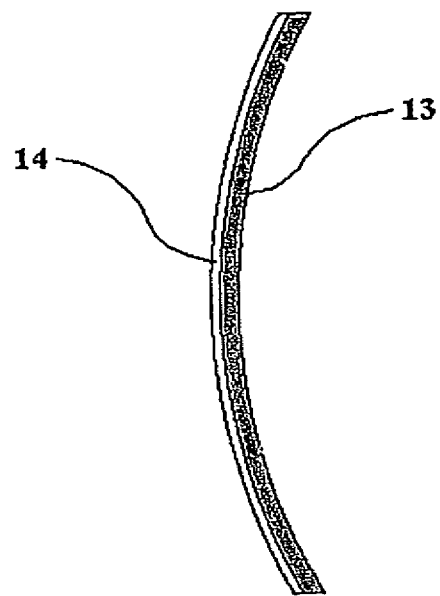
FIG. 5 is a view of the silicone device with laminated cloth for integration into a manufactured bra.

Referring now to FIG. 5, the present invention is shown as a single layered membrane 13 incorporated into or onto a layer of cloth 14.

Figure 6:
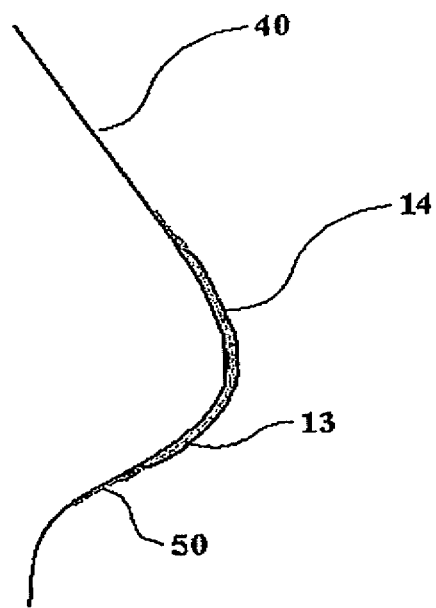
FIG. 6 is a view of the laminated cloth as an integrated part of a nursing bra shown on a wearer.

Referring now to FIG. 6, manufactured nursing bra 50 is shown as it would be used by a wearer.

What is claimed is:

1. A breast shield to cover a breast area of a user, the breast shield comprising:
a silicone rubber first layer adapted to contact the breast area of the user;
a silicone rubber second layer attached to an outer side of the first layer;
the second layer having a greater thickness than the first layer and a higher durometer than the first layer;
the first and second layers including similar sizes with outer edges being aligned with the second layer being thicker than the first layer at the outer edges;
the second layer forms a frame that supports the first layer.

2. The breast shield of claim 1, wherein the first layer is a gel.

3. The breast shield of claim 1, wherein the first and second layers include a combined thickness of 20-90 mils.

4. The breast shield of claim 1, wherein the shield is translucent.

5. The breast shield of claim 1, wherein an inner surface of the first layer is smooth to facilitate adherence to the breast area of the user.

6. The breast shield of claim 1, wherein the first and second layers each have an essentially circular shape.

7. The breast shield of claim 1, further comprising a third layer attached to an outer surface of the second layer away from the first layer, the third layer comprising a clothing item.

8. A breast shield to cover a breast area of a user, the breast shield comprising:
a silicone rubber first layer with a first surface adapted to contact the breast area of the user and a second surface;
a silicone rubber second layer attached to the second surface of the first layer and being sized relative to the first layer with the outer edges of the first and second layers being aligned, the second layer having a greater thickness and a higher durometer than the first layer throughout the first and second layers; and
a clothing item attached to the second layer away from the first layer, the clothing item positioning the first and second layers relative to the breast area of the user.

9. The breast shield of claim 8, further comprising an adhesive positioned between an outer surface of the second layer and an inner surface of the clothing item that attaches the clothing item to the second layer.

10. The breast shield of claim 9, wherein the adhesive comprises separate sections that are spaced apart along the outer surface of the second layer.

11. The breast shield of claim 8, wherein the clothing item includes a smaller thickness than the second layer.

12. The breast shield of claim 8, wherein the first and second layers are translucent.

13. The breast shield of claim 8, wherein the first surface of the first layer is smooth to facilitate adherence to the breast area of the user.

14. The breast shield of claim 8, wherein the first layer is a gel.

15. A breast shield to cover a breast area of a user, the breast shield comprising:
a multi-layered body sized to extend over the breast area of the user and including a gel first layer with a first side and a second side and a non-gel second layer positioned at the second side of the gel first layer, the first side of the first layer configured to contact against the breast area of the user, the first and second layers including aligned outer edges;
the non-gel second layer forms a frame that supports the gel first layer;
the gel first layer having a smaller thickness than the non-gel second layer at the outer edges.

16. The breast shield of claim 15, wherein the non-gel second layer is silicone rubber.

17. The breast shield of claim 15, wherein the gel first layer and the non-gel second layer are attached directly together.

18. The breast shield of claim 15, wherein each of the gel first layer and the non-gel second layer are translucent.

* * * * *